United States Patent [19]

Longley et al.

[11] Patent Number: 4,480,119

[45] Date of Patent: * Oct. 30, 1984

[54] UNSYMMETRICAL SULFOSUCCINATE DIESTERS

[76] Inventors: Kermit D. Longley, 305 Winnebago, Park Forest, Ill. 60466; Anastasios J. Karalis, 2300 N. Commonwealth Ave., Chicago, Ill. 60614

[*] Notice: The portion of the term of this patent subsequent to Sep. 26, 1995 has been disclaimed.

[21] Appl. No.: 49,384

[22] Filed: Jun. 18, 1979

Related U.S. Application Data

[63] Continuation-in-part of Ser. No. 842,199, Oct. 14, 1977, abandoned, which is a continuation of Ser. No. 535,764, Dec. 23, 1974, abandoned.

[51] Int. Cl.$^3$ .................................... C07C 143/12
[52] U.S. Cl. .................................... 560/151; 252/354; 252/545; 252/557; 524/747; 524/748; 544/110
[58] Field of Search .................... 560/151; 544/110; 252/354, 545, 557

[56] References Cited

U.S. PATENT DOCUMENTS

| | | | |
|---|---|---|---|
| 2,028,091 | 1/1936 | Jaeger | 560/151 |
| 4,039,562 | 8/1977 | Bloch et al. | 560/151 |
| 4,117,237 | 9/1978 | Longley et al. | 560/151 |

FOREIGN PATENT DOCUMENTS 2535800 3/1976 Fed. Rep. of Germany.

*Primary Examiner*—Vivian Garner

[57] ABSTRACT

Unsymmetrical sulfosuccinate diesters in which one carboxyl group of the sulfosuccinate is esterified with an alcohol, for instance, a $C_8$–$C_{12}$ aliphatic monohydric alcohol such as octyl or dodecyl alcohol, or with an ethoxylated or propoxylated alkyl phenol, and in which the other carboxyl group is esterified by reaction with ethylene oxide, and method of preparation of such diesters. The said diesters have utility as surfactants, such as detergents and emulsifiers.

7 Claims, No Drawings

UNSYMMETRICAL SULFOSUCCINATE DIESTERS

This application is a continuation-in-part of application Ser. No. 842,199, filed Oct. 14, 1977, now abandoned, which, in turn, is a continuation of application Ser. No. 535,764, filed Dec. 23, 1974, which latter application is now abandoned.

Our invention relates to the preparation of certain types of novel unsymmetrical sulfosuccinate diesters at least most of which can be represented by the following formula:

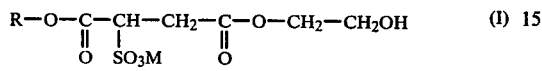

where R—O— is the radical of a $C_6$-$C_{20}$ aliphatic monohydric alcohol, or of an ethoxylated or propoxylated alkyl phenol in which there are at least one but not more than 3 nuclearly attached alkyl groups not more than 2 of which containing from 5 to 12 carbon atoms and the said such other alkyl group, or groups, as may be present, containing 1 to 3 carbon atoms, and in which the number of oxyethylene (—$C_2H_4O$) groups is from 1 to 12, or the number of propoxy (—$C_3H_6O$) groups is from 1 to 4; and wherein the terminal —$CH_2$—$CH_2OH$ group is derived from ethylene oxide; and M is a cation selected from the group of alkali metals (including ammonium), alkaline earth metals, and water-soluble organic amines. Most desirably, in the novel compounds of our present invention, R is alkyl containing from 8 to 15 carbon atoms.

It is particularly desirable that the novel sulfosuccinate compounds of our present invention be marketed and used in the form of the aforementioned types of salts, that is, where M is formula (I) is an alkali metal (which term is here used to mean sodium potassium, lithium and ammonium), or alkaline earth metals, namely, calcium, magnesium, strontium and barium; or, as noted above, water-soluble organic amines. These latter, which most advantageously are lower molecular weight amines, may be selected from a wide group, typical examples of which are dimethylamine; diethylamine, triethylamine; propylamine; monoisopropylamine, diisopropylamine, triisopropylamine, and commercial mixtures of said isopropylamines; butyl amine, amyl amine; monoisopropanolamine, diisopropanolamine, triisopropanolamine and commercial mixtures of said isopropanolamines; ethanolamines such as monoethanolamine, diethanolamine, triethanolamine, and commercial mixtures thereof; polyamines such as aminoethyl ethanolamine, ethylenediamine, diethylenetriamine, hydroxyethyl ethylenediamine, and hexamethylenediamine; hexylamine; cyclohexylamine; dimethylbenzyl-amine, benzylamine; morpholine; etc. Such salts can be prepared from sodium or potassium salts of the novel sulfosuccinate compounds of our present invention by known metathesis techniques.

Generally speaking, the radical R—O— in formula (I) will be derived from a long chain aliphatic monohydric alcohol, or an ethoxylated or propoxylated alkyl phenol containing a nuclearly attached alkyl group or groups each having a chain of from 5 to 12 carbon atoms, and the terminal —$CH_2$—$CH_2OH$ radical in said formula (I) is derived from ethylene oxide.

Particularly preferred embodiments of the novel compounds of our invention comprise unsymmetrical sulfosuccinate diesters one carboxyl group of the sulfosuccinate of which is esterified with a $C_8$-$C_{20}$ aliphatic monohydric alcohol, and the other carboxyl group of the sulfosuccinate of which is reacted with ethylene oxide to form an ethylene glycol ester group.

The aforesaid compounds are useful in various fields where surfactant or wetting-out properties are a desideratum such as, for instance, detergents, emulsifiers, penetrating agents, stabilizing agents, dispersants, emollients, and the like.

Sulfosuccinate surfactants and, more specifically, sulfosuccinate diesters, are known to the art, being disclosed, for instance, in U.S. Pat. Nos. 2,028,091; 2,252,401; 2,316,234; 2,507,030; 2,887,504; 2,976,208; 2,976,209; 2,976,211; 3,002,994; 3,080,280; 3,123,641; 3,141,905 and 3,155,591; and in French Patent of Addition No. 69,516; and in Ind. Eng. Chem., 33, 731-7 (1941) by C. R. Caryl. However, so far as we are aware, there has been no prior suggestion or disclosure of any of the compounds of our invention.

It may be noted that the aforesaid U.S. Pat. No. 2,028,091 (Jaeger), which discloses sulfosuccinate diesters, states that, in certain instances, ethylene oxide or similar alkylene oxides such as propylene oxide or butylene oxide can be esterified with acids such as maleic acid, and then adding the sulfo group, or by esterifying the sulfodicarboxylic acid with ethylene oxide. This is generally shown on page 2, col. 2, lines 36-42, and is exemplified by Example 19 of said Jaeger patent. Such compounds, in all such instances where ethylene oxide or similar alkylene oxide is suggested to be used, are described as being "complex" esters and their complexity is such that Jaeger does not describe, nor was he able to describe, what the structure of such complex esters actually may be, other than their being broadly characterized as comprising esters of sulfodicarboxylic acids. At any rate, they are not the unsymmetrical sulfosuccinate diesters of our present invention, and the latter cannot be produced by the aforesaid Jaeger procedures which result in his self-characterized complex esters. Moreover the unsymmetrical sulfosuccinate diesters of the present invention possess distinctly improved properties in relation to wetting properties, foaming properties and in other respects in comparison with such complex esters to which Jaeger refers as set forth above.

In the preparation of the novel compounds of our invention, maleic anhydride is initially reacted with a long chain aliphatic (which term includes cycloaliphatic) monohydric alcohol, or with an ethoxylated or propoxylated alkyl phenol, in proportions such as to produce predominately the maleic acid monoester. Generally speaking, a mole ratio of 1 to about 1.2 moles of maleic anhydride to 1 mole of the long chain aliphatic monohydric alcohol or of the alkyl phenol or of the ethoxylated or propoxylated alkyl phenol or of the ethoxylated or propoxylated alkyl phenol results in the production of a reaction product which contains upwards of 90 or 95% of the monoester. It is generally unnecessary to purify the reaction product to separate the monoester but this can be done, if desired, by conventional purification techniques.

In a particularly preferred procedure for the production of the monoester, particularly where the alcoholic reactant with the maleic anhydride is, for instance, a $C_8$ to $C_{16}$ aliphatic monohydric or fatty alcohol, said alcohol is initially admixed with a small proportion, commonly from about 0.05 to 0.5%, by weight of said alcohol, of an inorganic hydroxide or a basic catalyst, such as sodium hydroxide or potassium hydroxide in strong aqueous solution, and heated to a somewhat elevated temperature, for instance about 100°–115° C. under vacuum while purging with an inert gas, such as nitrogen, argon or helium, whereby to remove all or essentially all water from the system, after which the vacuum is released and the alcoholic reactant, at the selected temperature, is admixed with the maleic anhydride and reacted, for instance, at about 70° to about 100° C., until the acid number reaches or approximates that of the desired monoester or half ester. To said monoester is then added the ethylene oxide to drive the reaction to completion which, in the usual cases, involves the employment of about 0.2 to 0.3 moles excess to effect completion of the reaction in a reasonable length of time. To the resulting unsymmetrical diester there is then added slightly more than 1 mole of the bisulfite per mole of maleic anhydride used and the resulting mixture is heated until the reaction is complete. It should be noted that, in the preparation of the novel compounds of our present invention, whether by the preferred procedure described in this paragraph or otherwise in accordance with our invention, it is essential that maleic anhydride be utilized.

In the preparation of those of the compounds of our invention which are in the form of amine salts, it is sometimes desirable to produce such in substantially anhydrous form, soluble in organic solvents, particularly polar organic solvents such as ethyl alcohol, propyl alcohol, isopropyl alcohol, methyl and ethyl formamides, etc. To this end, for instance, the aforedescribed diesters can be reacted with a solution containing an organic amine, sufficient water to provide a reaction medium and containing dissolved sulfur dioxide to form a sulfite of said organic amine, and a water-miscible alcohol, for instance, methyl alcohol, ethyl alcohol, n-propanol or isopropyl alcohol, whereby to produce a substantially anhydrous organic amine salt of the said sulfosuccinic acid diesters. For best results, in carrying out such reaction, for each mol of said diester, the solution reacted therewith should contain about 1 mole or slightly more of organic amine or amines, and about 1 mole of water containing about 1 mol of sulfur dioxide.

In the preparation of the novel compounds of our invention by the foregoing method, is important, in order to obtain said compounds, that the sequence of steps noted above be followed, that is, that the maleic acid monoester of the $C_6$–$C_{20}$ aliphatic monohydric alcohol, or of the ethoxylated or propoxylated alkyl phenol, first be provided or prepared after which the reaction with the ethylene oxide is carried out, followed by the reaction with the aqueous bisulfite to introduce the sulfonic group into the molecule. Thus, for instance, if the ethylene oxide is first reacted with the maleic anhydride and then with (a) the $C_6$–$C_{20}$ aliphatic monohydric alcohol or ethoxylated or propoxylated alkyl phenol, followed by the reaction with the aqueous bisulfite, or (b) the aqueous bisulfite followed by the reaction with the $C_6$–$C_{20}$ aliphatic monohydric alcohol or the ethoxylated or propoxylated alkyl phenol, the products of or contemplated by the present invention are not obtained.

In the reaction of the monoesters with the ethylene oxide to produce the intermediate diesters which are then converted into the unsymmetrical sulfosuccinate esters of our invention, said reaction is especially desirably carried out in the presence of a catalyst, particularly a basic inorganic or organic material such as, by way of example, sodium hydroxide, potassium hydroxide, sodium carbonate, potassium carbonate; tertiary amines such as triethylamine and triisopropylamine, and quaternary ammonium salts such as tetramethyl ammonium hydroxide, tetraethyl ammonium hydroxide, benzyl trimethyl ammonium hydroxide and benzyl triethyl ammonium hydroxide. Such catalysts can be used in variable proportions, generally in the range of 0.1 to 2 or 3%, based on the weight of the monoester, depending generally on the basicity of the catalyst.

No novelty is claimed in the monoesters of maleic anhydride with certain of the alcohols as such, or in certain of the diesters, as such, since such compounds and various procedures for their preparation are known to the prior art, and the same is true with respect, per se, to certain of the reaction products of such half esters or monoesters with ethylene oxide as shown, for instance, in U.S. Pat. No. 3,270,088.

The radicals represented by R—O— in formula (I) can be derived from straight chain or branch chain aliphatic monohydric alcohols having the formula $R_1OH$ where $R_1O$— is the radial of a $C_6$–$C_{20}$ aliphatic monohydric alcohol, or of an ethoxylated or propoxylated phenol in which there are not more than 3 nuclearly attached alkyl groups each containing from 5 or 12 carbon atoms and in which the number of oxyethylene (—$C_2H_4O$) groups is from 1 to 12, or the number of propoxy (—$C_3H_6O$) groups is from 1 to 4.

The radicals represented by RO— in formula (I) can be straight chain or branch chain and include, by way of illustration, radicals derived from such alcohols as n-hexyl alcohol, isohexyl alcohol, cyclohexanol, cyclooctanol, 2-ethyl hexyl alcohol, 2-ethyl octyl alcohol, n-nonyl alcohol, isononyl alcohol, n-decyl alcohol, isodecyl alcohol, undecyl alcohol, n-dodecyl alcohol, isododecyl alcohol, tridecyl alcohol, tetradecyl alcohol, pentadecyl alcohol, hexadecyl alcohol, heptadecyl alcohol and octadecyl alcohol, and mixtures thereof as in commercial mixtures of fatty and other alcohols; oxo alcohols such as the primary monohydric saturated aliphatic $C_{10}$–$C_{20}$ alcohols as, for instance, oxo tridecyl alcohol and oxo hexadecyl alcohol (see U.S. Pat. No. 2,965,678), and they can be derived from grain sources, fatty triglycerides, and petroleum sources including kerosene fractions and polymerized olefins such as polypropylenes, for instance, propylene trimers and tetramers, from oxo alcohol procedures, and by Ziegler catalytic and other chemical procedures. Also included in such aliphatic monohydric alcohols are those derived by adducting 1 mole of such alcohols as hexyl, octyl, decyl and dodecyl alcohols, or analogous branched chain alcohols, with 1 to 12 moles of ethylene oxide, or by adducting 1 mole of such alcohols as hexyl, octyl, decyl or dodecyl alcohols, or analogous branched chain alcohols, with from 1 to 4 moles of propylene oxide.

Where R—O— in formula (I) is the radical of an ethoxylated or propoxylated alkyl phenol in which there are not more than 3 alkyl groups, as described hereinbefore, said alkyl phenol radicals can conveniently be represented by the formula

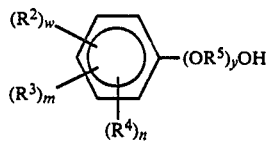

(II)

where $R^2$ and $R^3$ are the same or dissimilar $C_5$–$C_{12}$ alkyl radicals, $R^4$ is a $C_1$–$C_3$ alkyl radical, $R^5$ is $C_2H_4$ or $C_3H_6$; each of w, m and n is zero to 1, subject to the proviso that, when w is zero, m is 1 or 2; and y is 1 to 12 when $R^5$ is $C_2H_4$ and is 1 to 4 when $R^5$ is $C_3H_6$.

Illustrative examples of such ethoxylated and propoxylated alkyl phenols from which compounds of our invention can be prepared are the adduct of 1 mole of octyl phenol with 2 moles of ethylene oxide; the adduct of 1 mole of nonyl phenol with 3 moles of ethylene oxide; the adduct of 1 mole of nonyl phenol with 8 to 10 moles of ethylene oxide; the adduct of 1 mole of nonyl phenol with 1 mole of ethylene oxide; the adduct of 1 mole of nonyl phenol with 1 mole of propylene oxide; the adduct of 1 mole of diamyl phenol with 3 moles of ethylene oxide; the adduct of 1 mole of dodecyl phenol with 2 moles of ethylene oxide; the adduct of 1 mole of dioctyl phenol with 2 moles of propylene oxide; the adduct of 1 mole of dinonyl phenol with 3 moles of ethylene oxide; the adduct of 1 mole of nonyl hydroxy toluene with 2 moles of ethylene oxide; the adduct of 1 mole of isopropyl nonyl phenol with 2 moles of ethylene oxide; and the adduct of 1 mole of dinonyl isopropyl phenol with 3 moles of ethylene oxide.

Illustrative examples of chemical compounds falling within the scope of our invention are the following:

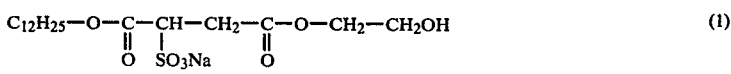

(1)

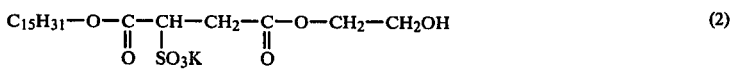

(2)

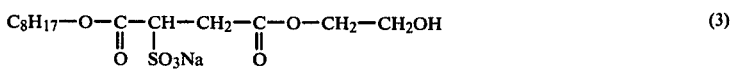

(3)

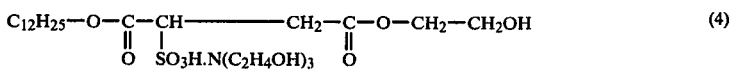

(4)

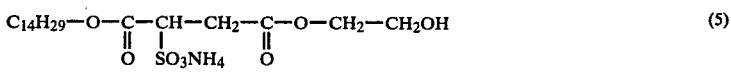

(5)

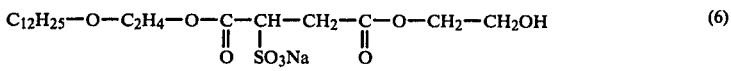

(6)

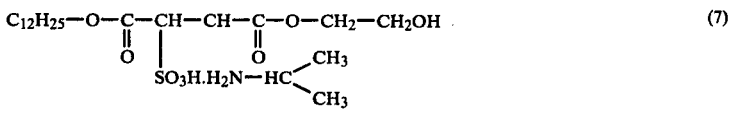

(7)

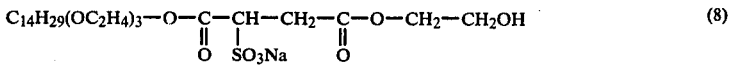

(8)

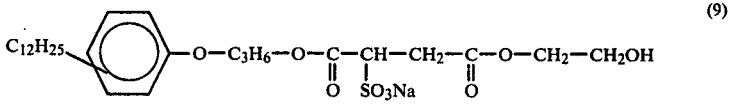

(9)

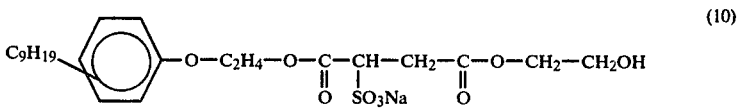

(10)

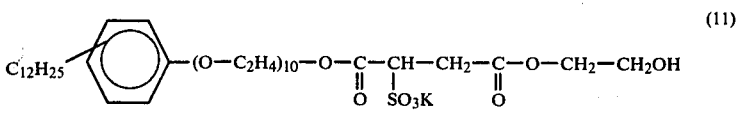

(11)

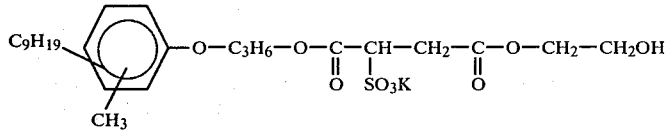

(12)

The following examples are illustrative of the preparation of typical compounds of the present invention. All temperatures recited are in degrees Centigrade.

EXAMPLE I (a) To 1242 g (6.06 moles) of "NEODOL 25" (a commercial product consisting mainly of a mixture of $C_{12}$–$C_{15}$ aliphatic monohydric alcohols having an average molecular weight of about 205) are added 1.4 g of KOH in 3 ml of water, and the mixture is heated to about 105° under a vacuum 25 mm. of Hg. while purging with gaseous nitrogen, and then held at such temperature for about ½ hour. It is then cooled to about 75°, the vacuum is released, and to it is added 600 g (6.12 moles) of maleic anhydride, and the reaction mixture is maintained at about 75° for approximately 2 hours at the end of which time the acid value is 3.47 meq/g. indicating formation of the maleic acid monoester of said mixture of alcohols.

(b) The monoester produced in part (a) hereof is placed in an autoclave heated to 100° and to it is added 345 g (7.85 moles) of ethylene oxide over a period of 5 hours, at the end of which time the acid value is 0.001 meq/g. The resulting diester contains, in the molecule, approximately 1.2–1.3 oxyethylene groups.

(c) To the diester produced in part (b) hereof there is added 600 ml of water and 1530 g of 42% aqueous sodium bisulfite solution (6.18 moles) and heated to 90°. An almost immediate exothermic reaction occurs and the pressure in the autoclave rises to of the order of 5 to 10 pounds per square inch. The reaction is complete in about ½ hour. A somewhat viscous, light yellow solution is obtained containing approximately 0.5% free sodium sulfite and 67% solids.

EXAMPLE II

To 500 g (3.7 moles) of "ALFOL 610" ($C_6$–$C_{10}$ synthetic alcohol, mean mol. wt. 136) is added 1 g of NaOH dissolved in 2 ml of water, and this mixture is heated to 85° in vacuo for ½ hour. To it is then added 361 g (3.7 moles) of maleic anhydride at 70° and the resulting reaction mixture is maintained at this temperature for 1 hour. At the end of this period, the acid value is 4.25 meq/g. The resulting monoester is placed in a stirred autoclave heated to 100° and to it is added 216 g (4.9 moles) of ethylene oxide over a period of 2 hours at 30 psi pressure, then stirred an additional 3 hours at this temperature. At this point the pressure in the autoclave is about 10 pounds per square inch. The acid value of the diester, which contains, in the molecule, approximately 1.3 oxyethylene groups, is 0.01 meq/g. The said diester is stripped in vacuo at 95°–100° and to it at this temperature is added 970 g of a 40% aqueous sodium bisulfite solution (3.7 moles) over a period of 1 hour, and to this solution is then added 345 ml of 95° water. The final sulfosuccinate product is a mobile liquid at room temperature which is completely soluble in water.

EXAMPLE III

To 400 ml of water are added 34 g of the sulfosuccinate surfactant prepared in Example II, 1.25 g of potassium persulfate, 7 g of hydroxyethyl cellulose ("Cellosize WP-09," Union Carbide Corporation), and 1.3 g of sodium bicarbonate. This solution is heated to 70° and to it is added at 70°–75°, in separate streams, over a period of 4 hours, 550 g of vinyl acetate and a solution of 1.25 g of sodium persulfate in 50 ml of water. When the addition is complete, the temperature is raised to 90° for ½ hour. The resulting vinyl acetate latex contains 55% solids and shows no separation after standing for 6 months.

EXAMPLE IV

The procedure described in Example I is carried out except that, in part (a), in place of the 1242 g of "NEODOL 25", there is used 1300 g (10 moles) of 2-ethylhexanol. The balance of Example I is carried out using 1000 g (10.2 moles) of maleic anhydride, 525 g (11.9 moles) of ethylene oxide, and 2600 g (10.5 moles) of 42% aqueous sodium bisulfite. The sulfosuccinate product obtained corresponds essentially to the formula

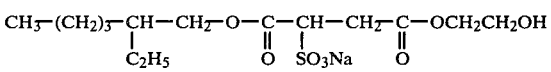

EXAMPLE V

The procedure described in Example II is carried out except that, in place of the 500 g of "ALFOL 610," there is used 1133 g (3.7 moles) of an adduct of 1 mole of nonyl phenol with 8 moles of ethylene oxide. The sulfosuccinate product obtained corresponds to the formula

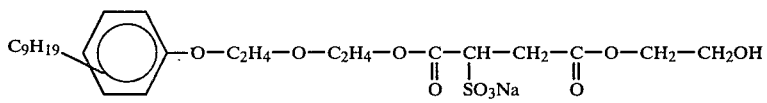

EXAMPLE VI

The procedure described in Example II is carried out except that, in place of the 500 g of "ALFOL 610," there is used 482 g (3.7 moles) of 2-ethyl hexanol. The sulfosuccinate product obtained is desirable for use in emulsion polymerization procedures such as are shown in Example III above.

EXAMPLE VII (a) To 450 g of "ALFOL 12" (a $C_{11}$–$C_{14}$ aliphatic synthetic alcohol) are added 243 g of maleic anhydride in the presence of 1.5 g of KOH and the mixture is heated to about 100° while purging with gaseous nitrogen and then held at that temperature for approximately 1 hour or until the resulting half-ester or monoester has an acidity of 3.65 me/g as against the theoretical acidity of 3.59 me/g.

(b) The half-ester of part (a) hereof is placed in an autoclave heated to about 100° and to it is gradually added 130 g of ethylene oxide over a period of about 5 hours at the end of which time the acid diester is produced having an acid value of 0.003 me/g.

(c) To the diester produced in part (b) hereof, 611 g of a 42% water solution of sodium bisulfite is added and then 250 cc. of water is added and reaction is effected as described in part (c) of EXAMPLE I. The resulting final product corresponded to the formula

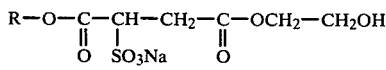

where R is the alkyl radical of the "ALFOL 12" alcohol. The composition, as produced, was a clear, lemon-colored pourable gel, having a wetting time, in the form of 0.5% aqueous solution, of 4 seconds, and exhibited a foam height, on shaking, in the form of a 0.3% aqueous solution, of 190 mm.

In a variant but less advantageous aspct of our invention, compounds are prepared in which the terminal essentially single —$CH_2$—$CH_2OH$ group is replaced by groups which contain not more than a total of 4 oxyethylene groups but, of course, in which the terminal group is —$C_2H_4OH$. Such compounds can be represented by the formula

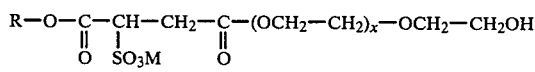
(III)

where x is an integer from 1 to not in excess of 3. Illustrations of such compounds are the following:

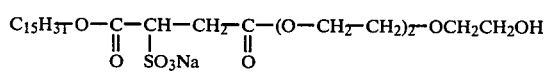
(13)

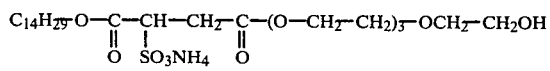
(14)

Such compounds are prepared simply by reacting the previously prepared, in the manner described, for instance, in EXAMPLE I, monoester by the procedure of part (a) thereof; and then, as in part (b) of said EXAMPLE I, by reacting with ethylene oxide but, instead of utilizing about 1 mole or slightly in excess of 1 mole of ethylene oxide, using a corresponding greater amount of ethylene oxide but not such an amount as to exceed that represented by the above formula (III), after which the sulfonic acid salt radical is introduced by following the procedure generally as described in part (c) of EXAMPLE I. Illustrative thereof is the following EXAMPLE VIII.

EXAMPLE VIII

EXAMPLE I is carried out in the manner described therein except that, in part (b) thereof, instead of 345 g of ethylene oxide, a total of 700 g of ethylene oxide is used, fed into the reaction mixture over a period of about 9 hours.

We claim:

1. An unsymmetrical sulfosuccinate surfactant according to the formula

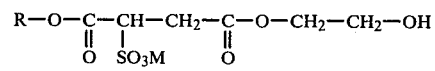

where R is a $C_6$-$C_{20}$ alkyl or a radical of an ethoxylated or propoxylated alkyl phenol having the following formula:

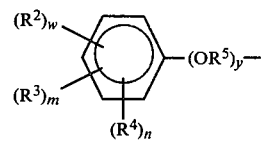

where $R^2$ and $R^3$ are the same or dissimilar $C_5$-$C_{12}$ alkyl radicals, $R^4$ is a $C_1$-$C_3$ alkyl radical, $R^5$ is $C_2H_4$ or $C_3H_6$ and each of w, m, and n is zero to 1, with the proviso that when w is zero, m is 1 or 2; when $R^5$ is $C_3H_6$, y is 1-4 and when $R^5$ is $C_2H_4$, y is 1 to 12; M is a cation selected from the group of alkali metals, alkaline earth metals, and water soluble organic amines.

2. A surfactant according to claim 1, in which R is alkyl containing from 8 to 16 carbon atoms.

3. A surfactant according to claim 2, in which R is a straight chain.

4. A surfactant according to claim 1, in which R—O— is

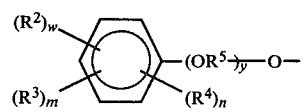

where $R^2$ and $R^3$ are the same or dissimilar $C_5$-$C_{12}$ alkyl radicals, $R^4$ is a $C_1$-$C_3$ alkyl radical, $R^5$ is $C_2H_4$ or $C_3H_6$, each of w, m and n is zero to 1, with the proviso that, when w is zero, m is 1 to 2; and y is 1 to 12 when $R^5$ is $C_2H_4$ and y is 1 to 4 when $R^5$ is $C_3H_6$.

5. A surfactant according to claim 1, in which R— is

where $R^5$ is $C_2H_4$, and y is 1 to 12.

6. A surfactant according to claim 1, in which R—O— is the radical of 2-ethyl hexyl alcohol and M is sodium.

7. An unsymmetrical sulfosuccinate surfactant according to the formula:

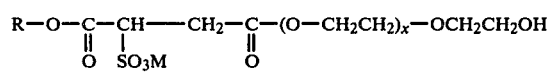

where R is a C$_6$–C$_{20}$ alkyl or a radical of an ethoxylated or propoxylated alkyl phenol having the following formula:

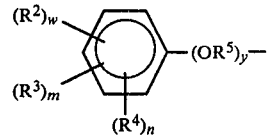

where R$^2$ and R$^3$ are the same or dissimilar C$_5$–C$_{12}$ alkyl radicals, R$^4$ is a C$_1$–C$_3$ alkyl radical, R$^5$ is C$_2$H$_4$ or C$_3$H$_6$ and each of w, m, and n is zero to 1, with the proviso that when w is zero, m is 1 or 2; when R$^5$ is C$_3$H$_6$, y is 1–4 and when R$^5$ is C$_2$H$_4$, y is 1 to 12, x is 1 to 3, and M is a cation selected from the group of alkali metals, alkaline earth metals, and water soluble organic amines.

* * * * *